United States Patent [19]
Gowan, Jr.

[11] Patent Number: 5,876,759
[45] Date of Patent: *Mar. 2, 1999

[54] RAPIDLY DISINTEGRATING PHARMACEUTICAL DOSAGE FORM AND PROCESS FOR PREPARATION THEREOF

[75] Inventor: Walter G. Gowan, Jr., Lansdale, Pa.

[73] Assignee: McNeil-PPC, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 842,597

[22] Filed: Apr. 16, 1997

Related U.S. Application Data

[63] Continuation of Ser. No. 566,649, Dec. 4, 1995, abandoned, which is a continuation of Ser. No. 97,806, Jul. 27, 1993, abandoned.

[51] Int. Cl.⁶ ........................................................ A61K 9/26
[52] U.S. Cl. .......................... 424/494; 424/470; 424/497
[58] Field of Search ..................... 424/470, 480, 424/482, 494, 497

[56] References Cited

U.S. PATENT DOCUMENTS

| | | | |
|---|---|---|---|
| 3,951,821 | 4/1976 | Davidson | 252/1 |
| 4,371,516 | 2/1983 | Gregory et al. | 424/22 |
| 4,851,226 | 7/1989 | Julian et al. | 424/441 |
| 4,855,326 | 8/1989 | Fuisz | 514/777 |
| 4,866,046 | 9/1989 | Amer | 514/159 |
| 4,873,085 | 10/1989 | Fuisz | 424/400 |
| 4,888,178 | 12/1989 | Rotini et al. | 424/468 |
| 4,997,856 | 3/1991 | Fuisz | 514/777 |
| 5,006,344 | 4/1991 | Jerzewski et al. | 424/465 |
| 5,028,632 | 7/1991 | Fuisz | 514/772 |
| 5,034,421 | 7/1991 | Fuisz | 514/772 |
| 5,037,657 | 8/1991 | Jones et al. | 424/466 |
| 5,073,384 | 12/1991 | Valentine et al. | 424/474 |
| 5,075,114 | 12/1991 | Roche | 424/470 |
| 5,075,291 | 12/1991 | DuRoss | 514/60 |
| 5,082,667 | 1/1992 | Van Scoik | 424/469 |
| 5,112,616 | 5/1992 | McCarty | 424/435 |
| 5,178,878 | 1/1993 | Wehling et al. | 424/466 |
| 5,204,115 | 4/1993 | Olinger et al. | 424/470 |
| 5,260,072 | 11/1993 | Roche et al. | 424/464 |
| 5,380,473 | 1/1995 | Bogue et al. | 264/11 |
| 5,387,431 | 2/1995 | Fuisz | 426/658 |
| 5,456,932 | 10/1995 | Fuisz et al. | 426/548 |
| 5,464,632 | 11/1995 | Cousin et al. | 424/465 |
| 5,501,858 | 3/1996 | Fuisz | 424/439 |
| 5,501,861 | 3/1996 | Makino et al. | 424/464 |
| 5,720,974 | 2/1998 | Makino et al. | 424/464 |

FOREIGN PATENT DOCUMENTS

| | | |
|---|---|---|
| 0 523 847 A1 | 1/1993 | European Pat. Off. . |
| WO 93/01805 | 2/1993 | WIPO . |

OTHER PUBLICATIONS

Physician's Desk Reference for Non–Prescription Drugs, 13th ed., Medical Economics Company, Inc. Montvale, NJ, pp. 413 and 590–1 (1992).

H.A. Lieberman et al., Pharmaceutical Dosage Forms: Tablets, 2nd ed., vol. 1, Marcel Dekker, Inc., New York, NY, pp. 367–377 (1989).

*Primary Examiner*—Jyothsan Venkat
*Attorney, Agent, or Firm*—Bernard F. Plantz

[57] ABSTRACT

The present invention relates to a compressed pharmaceutical dosage form containing pharmaceutical particles coated with a taste-masking composition, a water-disintegratable, compressible carbohydrate and a binder. These components are dry blended and compressed into a dosage form, such as a tablet, having a hardness sufficient to cause the carbohydrate to disintegrate within 30 seconds after oral administration, thereby allowing the coated particles to be swallowed.

16 Claims, No Drawings

RAPIDLY DISINTEGRATING PHARMACEUTICAL DOSAGE FORM AND PROCESS FOR PREPARATION THEREOF

This is a continuation of application Ser. No. 08/566,649, filed Dec. 4, 1995 now abandoned, which is a continuation of application Ser. No. 08/097,806, filed Jul. 27, 1993, now abandoned.

FIELD OF THE INVENTION

The present invention relates to a rapidly disintegrating pharmaceutical dosage form containing coated pharmaceutical particles and to a process for preparing such dosage forms.

BACKGROUND OF THE INVENTION

Rapidly disintegrating or dissolving pharmaceutical dosage forms are available for human patients who have difficulty swallowing conventional tablets or capsules, and for the sublingual and buccal administration of drugs.

Freeze-dried or lyophilized dosage forms are generally known to rapidly dissolve or disintegrate in the mouth. These forms consist of a porous matrix of a water-soluble or water-dispersible carrier material which is impregnated with a unit dose of the pharmaceutical active. These dosage forms are prepared by first adding the pharmaceutical active to a solution comprising the carrier material and a suitable solvent, typically water. The resulting composition is then subjected to a freeze drying procedure whereby the solvent sublimes under a high vacuum.

While freeze-dried dosage forms dissolve rapidly, they must be manufactured on expensive lyophilization equipment. Further, these dosage forms have generally only been used with water-insoluble actives that are relatively tasteless, because they disintegrate in the mouth, rather than being swallowed as in the case of conventional tablets and capsules.

Water-soluble drugs are generally avoided in freeze-dried dosage forms because of the dissolution of the drug in the mouth, which results in a bitter or otherwise objectionable taste. Further problems can arise when water-soluble drugs are used because of the formation of eutectic mixtures, which lower the freezing point of the formulation, resulting in incomplete freezing or melting during the freeze-drying process. This phenomenon results in product loss.

M. S. Amer in U.S. Pat. No. 4,866,046, issued Sep. 12, 1989, describes an aspirin tablet that rapidly dissolves in the oral, preferably sublingual, cavity within 2–60 seconds. This tablet provides rapid absorption of aspirin from the saliva into the blood stream. The sublingual tablet is prepared by compressing into slugs a mixture of starch (10% moisture), acetylsalicylic acid, flavor and sweetener. The slugs are then ground (14–16 Mesh size) and recompressed into tablets. An amino acid may also be used with the aspirin for its solubilizing and a taste-neutralizing effects.

U.S. Pat. No. 5,082,667, issued Jan. 21, 1992, to K. G. Van Scoik discusses a tablet triturate dosage that quickly dissolves quickly in the buccal cavity. The form includes a porous, cementatory network of a water-soluble but ethanol-insoluble carbohydrate, which contains discrete particles of the active ingredient that have been coated with a triglyceride coating. The discrete particles are prepared by suspending the active ingredient in molten triglyceride. The discrete particles are mixed with the carbohydrate and a temporary liquid binder to form a damp mass. The mass is then shaped into a tablet and dried to form the tablet triturate.

The tablet triturate of Van Scoik is limited to active ingredients, such as estazolam, that are not sensitive to the melting temperature of the triglyceride. Further, since the dosage form is formed into a damp mass and subsequently dried, conventional, compression tableting machines cannot be used to manufacture this product.

J. A. McCarty, in U.S. Pat. No. 5,112,616, issued May 12, 1992, discusses a fast dissolving buccal tablet containing a buccally absorbable active ingredient, a pharmaceutically acceptable lubricant and a soluble, directly compressible tablet excipient, such as sucrose or lactose. These ingredients are mixed together and compressed into the final tablet form. Since the active ingredient is not coated, patient compliance, especially in children, would be an issue if the pharmaceutical had a bitter or otherwise objectional taste.

A need, therefore, exists for a rapidly disintegrating dosage form containing taste-masked pharmaceutical particles that can be manufactured without the use of water or solvents, and compressed on conventional tableting machines. This dosage form should be suitable for use with both water-soluble and water-insoluble actives which may have an objectional taste.

SUMMARY OF THE INVENTION

The present invention provides a compressed pharmaceutical dosage form containing at least one pharmaceutical particle coated with a taste-masking composition, a water-disintegratable, compressible carbohydrate and a binder. These components are dry blended and compressed into a mass, such as a tablet, having a hardness sufficient to cause the carbohydrate to disintegrate within 30 seconds after oral administration, thereby allowing the coated pharmaceutical particle to be swallowed.

In a preferred embodiment, the pharmaceutical is coated with a blend of a first polymer selected from the group consisting of cellulose acetate and cellulose acetate butyrate and a second polymer selected from the group consisting of polyvinyl pyrrolidone and hydroxypropyl cellulose, where the weight ratio of the first polymer to the second polymer is within the range of about 90:10 to about 50:50.

In a further preferred embodiment of the present invention, the compressed pharmaceutical dosage form is prepared by coating the pharmaceutical with the aforementioned blend of first and second polymers in a fluidized bed coating operation. The coated pharmaceutical is dry blended with the water-disintegratable, compressible carbohydrate and the binder, and then compressed into a wafer having a hardness within the range of about 1.0 to about 3.0 kp, whereby the carbohydrate disintegrates after oral administration allowing said coated pharmaceutical to be swallowed.

DETAILED DESCRIPTION OF THE PREFERRED EMBODIMENTS

The compressed pharmaceutical dosage forms of the present invention rapidly disintegrates when contacted by water, saliva and aqueous solutions, and are particularly useful in the oral delivery of drugs. As used in the present invention "disintegrate" includes both the dissolution and dispersion of the dosage form when contacted with the aforementioned fluids. These dosage forms generally disintegrate in the mouth within about 30 seconds, and preferably within about 20 seconds or less.

The dosage forms contain coated particles comprising at least one pharmaceutical coated with a taste-masking coating, a water-disintegratable, compressible carbohydrate, and a binder. These ingredients are dry blended and then compressed into a mass, preferably a wafer, having a hardness sufficient to cause the carbohydrate to disintegrate after oral administration. Upon disintegration, the coated pharmaceutical particles are released from the dosage form with no objectionable taste and swallowed by the user.

Conventional tableting machines can be used to compress the ingredients into the final dosage form. Since the ingredients are dry blended, water-soluble, as well as water-insoluble, coated pharmaceuticals can be used in the dosage form. Further, in view of the use of a taste-masking coating, pharmaceuticals having an objectional taste may also be used in the present invention.

The water-disintegratable, compressible carbohydrate used in the present invention includes carbohydrate materials conventionally used in tablets. The carbohydrates facilitate the breakup of the dosage form after oral administration, and are described in Liberman et al., *Pharmaceutical Dosage Forms*, Marrel Dekker, Inc., New York, 2 Ed. Vol. 1, pp. 205–209 (1990), which is hereby incorporated by reference. Preferred water-disintegratable, compressible carbohydrates include mannitol, sorbitol, dextrose, sucrose, xylitol, lactose, and mixtures thereof.

The binder in the present invention is used to add cohesiveness to the formulation, thereby providing the necessary bonding to form a cohesive mass or compact upon compression. These binders are conventionally used in direct compression tablets and are described in Liberman et al., *Pharmaceutical Dosage Forms*, 2 Ed., Vol. 1, pp. 209–214 (1990), which is hereby incorporated by reference. Preferred binders include cellulose, cellulosic derivatives, polyvinyl pyrrolidone, starch, modified starch, and mixtures thereof, and, in particular, microcrystalline cellulose available from FMC Corp. under the trademark AVICEL® PH 101.

The dosage form of the present invention contains a coated particle containing at least one pharmaceutical active coated with a taste-masking coating. The active may be coated with taste-masking coatings known in the art, such as those described in U.S. Pat. No. 4,851,226, issued Jul. 25, 1989, to T. W. Julian, et al.,; U.S. Pat. No. 5,075,114, issued Dec. 24, 1991 to E. J. Roche; and commonly assigned U.S. application Ser. No. 715,949, filed Jun. 14, 1991 now abandoned, all of which are hereby incorporated by reference. As used in the present invention, "coated particle" refers to a solid pharmaceutical in the form of a crystal or particle, an agglomerate of individual particles, or a granuled particle, which has been coated with a the taste-masking composition. The dosage form may provide for immediate or sustained release of the pharmaceutical active.

Taste-masking compositions suitable for use as coatings are provided in the following Table:

| Polymer System | Coat Level[1] | Polymer Ratio[2] |
| --- | --- | --- |
| Cellulose Acetate/PVP | 5–60% | 90/10 to 60/40 |
| Cellulose Acetate Butyrate/PVP | 5–60% | 90/10 to 60/40 |
| Cellulose Acetate/HPC | 5–60% | 90/10 to 50/50 |
| Cellulose Acetate Butyrate/HPC | 5–60% | 90/10 to 50/50 |
| Cellulose Acetate/EUDRAGIT E 100 | 8–60% | All ratios |
| Cellulose Acetate Butyrate/EUDRAGIT E 100 | 8–60% | All ratios |
| Ethyl Cellulose/PVP | 8–60% | 90/10 to 60/40 |
| Ethyl Cellulose/HPC | 8–60% | 90/10 to 50/50 |
| Ethyl Cellulose/EUDRAGIT E 100 | 8–60% | All ratios |
| HPC | 10–60% | NA |
| HEC | 10–60% | NA |
| EUDRAGIT E 100 | 10–60% | NA |
| HPMC | 10–60% | NA |
| HEC/HPMC | 10–60% | All ratios |
| HPC/HPMC | 10–60% | All ratios |
| HEC/HPC | 10–60% | All ratios |
| 2-vinyl pyrridine styrene co-polymer | 10–60% | NA |
| CA/2-vps | 8–60% | All ratios |
| CAB/2-vps | 8–60% | All ratios |
| Ethyl Cellulose/2-vps | 8–60% | All ratios |
| Cellulose Triacetate/PVP | 8–60% | 90/10 to 60/40 |
| Cellulose Triacetate/HPC | 8–60% | 90/10 to 50/50 |
| Cellulose Triacetate/EUDRAGIT E 100 | 8–60% | All ratios |

[1]Percent by weight of the coated particle in a dried state.
[2]By weight.
PVP - polyvinylpyrrolidone
HPC - Hydroxypropyl cellulose
HEC - Hydroxyethyl cellulose
HPMC - Hydroxypropylmethyl cellulose
CA - Cellulose Acetate
CAB - Cellulose Acetate Butyrate
2-VPS - 2-Vinyl pyridine styrene
EUDRAGIT ™ E 100 - methylaminoethyl-methacrylate and neutral methacrylic acid esters available from Rohm Pharma GmbH, Germany.

Substantially all of the pharmaceutical or granulated pharmaceutical should be coated with a layer of taste-masking composition having a thickness of about 3 to about 10 microns. The coating should be substantially free of cracks, holes or other imperfections when examined under a scanning electron microscope at 100–500×.

The pharmaceutical active is preferably coated with a blend of a first polymer selected from the group consisting of cellulose acetate and cellulose acetate butyrate and a second polymer selected from the group consisting of polyvinyl pyrrolidone and hydroxypropyl cellulose. The weight ratio of the first polymer to the second polymer in this blend is within the range of about 90:10 to about 50:50 and preferably about 90:10 to about 70:30.

The first polymer of the blend is generally water-insoluble, but is soluble in organic solvents. These polymers provide good taste-masking properties since they do not dissolve in the mouth. However, if used alone, they do not provide adequate bioavailability of the pharmaceutical. To provide the requisite bioavailability, the second polymer, which is soluble in both water and organic solvents, is added to the blend that is used to coat the pharmaceutical active. This blend of first and second polymers provides the balance needed for the taste masking.

Preferred blends of the first and second polymers include cellulose acetate (CA) and polyvinyl pyrrolidone (PVP) having a weight ratio of CA:PVP within the range of about 90:10 to about 60:40, cellulose acetate (CA) and hydroxypropyl cellulose (HPC) having a weight ratio of CA:HPC within the range of about 90:10 to about 50:50, cellulose acetate butyrate (CAB) and hydroxypropyl cellulose (HPC) having a weight ratio of CAB:HPC within the range of about 90:10 to about 50:50, and cellulose acetate butyrate (CAB) and polyvinyl pyrrolidone (PVP) having a weight ratio of CAB:PVP within the range of about 90:10 to about 60:40.

Cellulose acetate NF powder, e.g., CA 398-10, CA 320-S or CA 435-75S available from FMC Corp., may be used as the first polymer in the blend. CA 398-10 polymer has an acetyl content of about 39.8 weight percent, a hydroxyl content of about 3.4 weight percent, a degree of substitution of 2.7 and a solution viscosity of about 38 poises or 10 seconds, as determined by ASTM Method D 1343 in the solution described as Formula A, ASTM Method D 871. The typical weight average molecular weight, according to the manufacturer, is 177,000 and the typical number average molecular weight is 58,500. CA 320-S polymer has an acetyl content of about 32.0 weight percent, a hydroxyl content of about 9.0 weight percent and a degree of substitution of 2.1. In a solution of 90:10 $CH_2Cl_2$:methanol, at 4% (w/w) concentration, the viscosity is 50 centipoise. The typical weight average molecular weight is 100,500 and the typical number average molecular weight is 63,500. CA 435-75S has an acetyl content of about 43.6 weight percent and a hydroxyl content of about 0.9 weight percent.

Cellulose acetate butyrate, e.g., CAB 171-15S, CAB 381-2 and CAB 500-1 available from FMC Corp., may also be used as the first polymer. CAB 171-15S has a butyryl content of 17 weight percent, an acetyl content of 29.5 weight percent, a hydroxyl content of 1.5 weight percent and a viscosity of 24 centipoises in a 4 weight percent solution of methylene chloride:methanol (90:10) one day after solution preparation at 25° C. CAB 381-2 has a butyryl content of 37 weight percent, an acetyl content of 13 weight percent and a hydroxyl content of 1.5 weight percent. CAB 500-1 has a butyryl content of 50 weight percent, an acetyl content of 5 weight percent and a hydroxyl content of 0.5 weight percent.

Polyvinyl pyrrolidone (Povidone USP), e.g., PLASDONE® K-25, K-25/28 or K-29/32 from ISP Corporation, may be used as the second polymer in the blend. Povidone K-25 has a viscosity of 2.4 centipoises in a 5% solution of water at a pH 7 and 25° C.

Hydroxypropyl cellulose, e.g., KLUCEL EF, JF and LF, available from Aqualon Co. may also be used a the second polymer. These polymers generally have a molecular weight of about 80,000 to about 370,000.

The blend of first and second polymers may be coated directly onto the pure pharmaceutical or may be coated onto a granulated particle containing the pharmaceutical. In the case of a granulated particle, such as a rotogranulated particle, the pharmaceutical active will constitute from about 5 to about 90 weight percent of the particle, with the remainder being the binder or filler. Suitable binders for the granulated particles include polyvinyl pyrrolidone, hydroxypropylmethyl cellulose, hydroxypropyl cellulose, and other pharmaceutically acceptable polymers. Fillers suitable for use in such granulated particles include lactose, confectioner's sugar, mannitol, dextrose, fructose, other pharmaceutically acceptable saccharides and microcrystalline cellulose.

The coated particles are prepared by spraying an organic solvent solution of the polymeric blend onto the pharmaceutical, or a granulated particle containing the pharmaceutical, in a fluidized bed, such as a Wurster coater or a rotogranulator. A wide variety of organic solvents may be used to prepare the solution of the polymeric blend. For example, a preferred solvent is a mixture of acetone and methanol, but other solvent systems may be employed, including methylene chloride, methylene chloride-methanol, acetone-ethyl acetate, toluene-ethanol and acetone-ethanol. Generally, the proportion of the polymer blend in the solvent solution will be within the range of about 5 to about 20, preferably about 8 to about 15, weight percent, depending on the solvent and other similar considerations.

When a fluidized bed coating operation is used, air, which may be heated, passes through a bed of the pharmaceutical solids to fluidize them, and the solution of the polymeric blend is sprayed onto the fluidized bed and thereby coats the pharmaceutical. The air passing through the bed dried the coating onto the pharmaceutical, so that a dry coated granule is obtained.

Conventional fluidized bed coating equipment is used in the present invention to coat the pharmaceutical or the rotogranulated particle containing the pharmaceutical. This equipment includes Wurster fluid-bed coaters, where the solution of the polymer blend is sprayed from the bottom of the chamber, and a rotogranulator, where the solution of the polymer blend is tangentially sprayed. These coating operations are further described in Liberman et al., *Pharmaceutical Dosage Forms*, Marrel Dekker, Inc., New York, Vol. 3, pp. 138–150 (1990), which is hereby incorporated by reference.

The coated particle, in a dried state, generally contains about 5 to about 60, preferably about 10 to 40, weight percent of the blend of the first and second polymers. The exact proportions of the coating to the pharmaceutical can, however, vary depending upon the level of taste-masking required and whether a sustained or immediate release of the pharmaceutical is desired. Larger proportions of the coating tend to provide a sustained release effect and enhance taste-masking.

The dosage form of the present invention may be used to orally administer a wide variety of solid pharmaceutical actives. Pharmaceutical actives which can be used in the dosage form include acetaminophen, ibuprofen, flurbiprofen, naproxen, aspirin, pseudoephedrine, phenylpropanolamine, chlorpheniramine maleate, dextromethorphan, diphenhydramine, famotidine, loperamide, ranitidine, cimetidine, astemizole, terfenadine, terfenadine carboxylate, cetirizine, mixtures thereof and pharmaceutically acceptable salts thereof.

The pharmaceutical(s) present in the dosage form in a present in a therapeutic effective amount, which is an amount that produces the desired therapeutic response upon oral administration and can be readily determined by one skilled in the art. In determining such amounts, the particular compound being administered, the bioavailability characteristics of the pharmaceutical, the dose regime, the age and weight of the patient, and other factors must be considered.

The dosage form may also contain ingredients other than the coated particles, carbohydrate and binder. The additional ingredients include sweeteners, such as aspartame, sucralose and saccharin; and lubricants, such as magnesium stearate, stearic acid, talc, and waxes. The dosage form may also incorporate pharmaceutical acceptable adjuvants. Such adjuvants, include, for example, preservatives, flavors, antioxidants, surfactants, and/or colors.

The compressed dosage form, on a dry basis, generally comprises from about 0.1 to about 45, preferably about 12 to about 25, percent by weight of the coated pharmaceutical particle; from about 30 to about 90, preferably about 40 to about 65, percent by weight of the water-disintegratable, compressible carbohydrate material; from about 1 to about 30, preferably about 5 to about 20, percent by weight of the binder; from about 0.1 to about 5, preferably about 0.1 to about 0.5, percent by weight of the lubricant; from about 0.05 to about 5, preferably about 0.1 to about 3.0, percent by weight of the sweetener; from about 0.05 to about 5, preferably about 0.2 to about 2.0, percent by weight of the flavor; and from about 0.01 to about 5, preferably about 0.03 to about 0.3, percent by weight of the color.

The unit weight of the dosage form will vary depending on the dosage of the active ingredient. The unit weight will generally range from about 250 to about 1500, preferably about 250 to about 1000, mg. A typical dosage form may contain:

| Ingredient | Unit Wt. (mg) |
| --- | --- |
| Coated Pharmaceutical Particle | 0.5–600 |
| Compressible Carbohydrate | 250–750 |
| Binder | 20–100 |
| Lubricant | 4–10 |
| Sweetner | 1–10 |
| Flavor | 1–10 |
| Color | 1–10 |

In a preferred embodiment of the invention, the dosage form has a size, shape, weight and hardness that allows for it to be introduced into the oral cavity and placed on the tongue, so as to rapidly disintegrate. Generally, the dosage form will be a tablet having a coin-shaped disc or wafer configuration. Preferably, the wafer will have a diameter of about 7/16 to about 3/4, preferably about 5/8, inch and a thickness of about 0.05 to about 0.5, preferably about 0.08 to 0.25, inch. While a wafer shape is generally preferred, because it provides a larger surface area to be contacted by the tongue and other moist areas of the oral cavity, other shapes may be employed, such as a cube, triangle and cylinder.

The dosage form is prepared by forming the coated particles of the pharmaceutical using the aforementioned techniques. The particle size of the coated particles, as well as the remaining components, is generally less than 400, preferably less than 150, microns. Larger particle sizes tend to give the wafer a gritty mouth feel, and should therefore be avoided. The components of the dosage form are then dry mixed to form a uniform powder blend. The blend is then compressed into a mass having the desired shape and hardness using conventional compression tableting techniques.

The external pressure applied by the tablet press during the compression step is controlled so that the hardness of the dosage form is within the range of about 1.0 to about 3.0, preferably about 1.5 to about 2.5, kp (kiloponds). This hardness is measure by conventional pharmaceutical hardness testing equipment, such as a Schleuniger Hardness Tester. Hardnesses within this range provide a dosage form which will rapidly disintegrate when placed in the oral cavity. If the hardness exceeds 3.0 kp, the compressed dosage form will not readily disintegrate in the oral cavity, while hardnesses less than 1.0 kp result in a dosage form exhibiting high friability.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE

This Example provides a formulation for making a rapidly disintegrating, compressed wafer that contains acetaminophen coated with a blend of cellulose acetate and polyvinyl pyrrolidone. The weights provided hereinafter are based on a wafer unit weight of 400 mg.

A coating solution containing a blend of cellulose acetate (CA 398-10) and polyvinyl pyrrolidone (Povidone 29/32) was prepared at 12% solids with an acetone/methanol (80:20) solvent. The ratio of cellulose acetate to polyvinyl pyrrolidone was 85:15.

Four kilograms of acetaminophen (nominal particle size of 300 microns) was charged into a Wurster (bottom spray) fluidized bed coating apparatus. The acetaminophen was then placed in a fluidized state by a flow of air at a temperature of 30° C. The coating solution was then sprayed (atomization air pressure=3 bar) onto the fluidized acetaminophen particles at a rate of 80 grams/min. until a coated acetaminophen particle containing approximately 12% by weight of the coating was obtained.

The coated acetaminophen particles were combined with following ingredients to produce the wafers:

| Ingredients | Unit Wt. (mg) |
| --- | --- |
| CA/PVP Coated Acetaminophen Particles | 91.0 |
| Mannitol (Granular), USP | 229.15 |
| Microcrystalline Cellulose, NF | 60.0 |
| Aspartame, NF | 6.0 |
| Prosweet Powder (Sugarless) | 1.5 |
| Color | 0.9 |
| Citric Acid, USP | 3.0 |
| Flavors | 5.2 |
| Colloidal Silicon Dioxide | 0.25 |
| Stearic Acid, NF | 3.0 |
| Wafer Weight | 400.0 |

Dry Blending

1. Screen the color through a 60 mesh screen, the CA/PVP coated acetaminophen particles through a 30 mesh screen and the mannitol through a 12 mesh screen.

2. Mix the microcrystalline cellulose, aspartame, flavors, citric acid, Prosweet, colloidal silicon dioxide and stearic acid by shaking in a container for two minutes.

3. Blend the color and mannitol in a blender.

4. Place the mixture from Step 2 and the CA/PVP coated acetaminophen particles in blender containing the mixture from Step 3 and blend.

Tablet Compression

1. Compress the blend into wafers to the following specifications on a rotary tablet press equipped with the following tooling:

Punches: 5/8 inch, flat faced, bevel edge

Dies: 5/8 inch round

Group Weight (10 wafers): Target—4.0 grams
  (Range: 360–440 milligrams)

Thickness: Target 2.0 mm (Range 1.8 to 2.2 mm)

Hardness: Target 2 kp (Range 1.5 to 2.5 kp)

2. Collect compressed wafers into a properly labelled container.

A wafer was placed in on the tongue of a human and was found to disintegrate in less than 30 seconds without a bitter aftertaste.

Various modifications can be made from the above-described embodiments without departing from the spirit and scope of the present invention.

What is claimed is:

1. A compressed pharmaceutical dosage form, comprising:

at least one coated particle comprising at least one pharmaceutical coated with a taste-masking coating comprising a blend of a first polymer selected from the group consisting of a cellulose acetate and cellulose acetate butyrate and a second polymer selected from the group consisting of polyvinyl pyrrolidone and hydroxypropyl cellulose, wherein the weight ratio of the first polymer to the second polymer is within the range of about 90:10 to about 50:50;

a water-disintegrateable, compressible carbohydrate selected from the group consisting of mannitol, sorbitol, dextrose, sucrose, xylitol, lactose and mixtures there of; and a binder selected from the group consisting of cellulose, polyvinyl pyrrolidone, starch, modified starch and mixtures there of, said dosage form having a hardness of about 1.0 to 3.0 kp wherein said carbohydrate disintegrate in the oral cavity within 30 second after oral administration thereby allowing said coated particle to be swallowed.

2. The pharmaceutical dosage form of claim 1 wherein the coated particles comprises about 5 to about 60 percent by weight of the blend of first and second polymers.

3. The pharmaceutical dosage form of claim 1 wherein the pharmaceutical is selected from the group consisting of acetaminophen, ibuprofen, flurbiprofen, naproxen, aspirin, pseudoephedrine, phenylpropanolamine, chlorpheniramine maleate, dextromethorphan, diphenhydramine, famotidine, loperamide, ranitidine, cimetidine, astemizole, terfenadine, terfenadine carboxylate, cetirizine, mixtures thereof and pharmaceutically acceptable salts thereof.

4. The pharmaceutical dosage form of claim 3 wherein the pharmaceutical is selected from the group consisting of acetaminophen, ibuprofen, loperamide, famotidine and aspirin.

5. The pharmaceutical dosage form of claim 1 wherein the blend comprises cellulose acetate and polyvinyl pyrrolidone.

6. The pharmaceutical dosage form of claim 1 wherein the blend comprises cellulose acetate and hydroxy-propyl cellulose.

7. The pharmaceutical dosage form of claim 1 wherein the blend comprises cellulose acetate butyrate and hydroxypropyl cellulose.

8. The pharmaceutical dosage form of claim 1 wherein the blend comprises cellulose acetate butyrate and polyvinyl pyrrolidone.

9. The pharmaceutical dosage form of claim 1 wherein the blend of first and second polymers is sprayed onto the pharmaceutical in a fluidized bed.

10. A compressed pharmaceutical wafer, comprising:

coated particles comprising at least one pharmaceutical coated with a blend of a first polymer selected from the group consisting of a cellulose acetate and cellulose acetate butyrate and a second polymer selected from the group consisting of polyvinyl pyrrolidone and hydroxypropyl cellulose, wherein the weight ratio of the first polymer to the second polymer is within the range of about 90:10 to about 50:50;

a water-disintegratable, compressible carbohydrate selected form the group consisting of mannitol, sorbitol, dextrose; sucrose, xylitol, lactose, and mixtures thereof; and a binder selected form the group consisting of cellulose, polyvinyl pyrrolidone, starch, modified starch and mixtures thereof, said wafer having a hardness within the range of about 1.0 to about 3.0 kp whereby said carbohydrate disintegrates in the oral cavity within 30 seconds after oral administration allowing said coated particles to be swallowed.

11. The wafer of claim 10 having a diameter of about 7/16 to about 3/4 inch, a thickness of about 0.05 to about 0.5 inch, and a hardness of about 1.5 to about 2.5 kp.

12. The wafer of claim 11 comprising:

about 0.5 to about 600 mg of said coated particles;

about 250 to about 750 mg of said carbohydrate; and about 20 to about 100 mg of said binder.

13. The wafer of claim 12 further comprising:

about 4 to about 60 mg of a lubricant;

about 1 to about 10 mg of a color;

about 1 to about 10 mg of a sweetener; and about 1 to about 10 of a flavor.

14. The wafer of claim 12 wherein the coated particle comprises about 5 to about 60 percent by weight of the blend of first and second polymers.

15. The wafer of claim 14 wherein the pharmaceutical is selected from the group consisting of acetaminophen, ibuprofen, flurbiprofen, naproxen, aspirin, pseudoephedrine, phenylpropanolamine, chlorpheniramine maleate, dextromethorphan, diphenhydramine, famotidine, loperamide, ranitidine, cimetidine, astemizole, terfenadine, terfenadine carboxylate, cetirizine, mixtures thereof and pharmaceutically acceptable salts thereof.

16. The wafer of claim 15 wherein the pharmaceutical is selected from the group consisting of acetaminophen, ibuprofen, loperamide, famotidine and aspirin.

* * * * *